United States Patent [19]

Pomeroy

[11] Patent Number: 5,645,056
[45] Date of Patent: *Jul. 8, 1997

[54] VARIABLE VOLUMETRIC INFLATABLE PUMP

[75] Inventor: Paul E. Pomeroy, Lake Elsinore, Calif.

[73] Assignee: Survival Resources, Inc., Lake Elsinore, Calif.

[*] Notice: The term of this patent shall not extend beyond the expiration date of Pat. No. 5,297,944.

[21] Appl. No.: 216,182

[22] Filed: Mar. 22, 1994

Related U.S. Application Data

[63] Continuation-in-part of Ser. No. 909,756, Jul. 7, 1992, Pat. No. 5,297,944.

[51] Int. Cl.⁶ .................. A62B 7/00; F04B 17/00; F04B 35/00; F04B 43/08
[52] U.S. Cl. .................. 128/205.13; 128/205.14; 128/205.16; 417/437; 417/328; 417/478; 92/91; 2/DIG. 3
[58] Field of Search .................. 128/205.13, 205.14, 128/205.16; 417/328, 437, 478; 92/91; 2/DIG. 3; 5/454

[56] References Cited

U.S. PATENT DOCUMENTS

| | | |
|---|---|---|
| 513,924 | 1/1894 | Hartnett .................. 128/205.16 |
| 527,248 | 10/1894 | North . |
| 2,068,134 | 1/1937 | Houghton . |
| 2,369,736 | 2/1945 | Hurt . |
| 2,686,006 | 8/1954 | Hasselquist . |
| 3,042,941 | 7/1962 | Marcus . |
| 3,046,978 | 7/1962 | Lea .................. 128/205.13 |
| 3,063,620 | 11/1962 | Black . |
| 3,068,494 | 12/1962 | Pinkwater . |
| 3,112,502 | 12/1963 | Forsberg . |
| 3,473,529 | 10/1969 | Wallace .................. 128/205.13 |
| 3,583,008 | 6/1971 | Edwards . |
| 3,676,276 | 7/1972 | Hirshen et al. . |
| 4,003,098 | 1/1977 | Fink . |
| 4,280,489 | 7/1981 | Johnson, Jr. . |
| 4,287,920 | 9/1981 | Johnson, Jr. . |
| 4,521,166 | 6/1985 | Phillips . |
| 4,531,330 | 7/1985 | Phillips . |
| 4,532,923 | 8/1985 | Flynn .................. 128/205.13 |
| 4,628,945 | 12/1986 | Johnson, Jr. . |
| 4,898,166 | 2/1990 | Rose et al. .................. 128/205.13 |
| 4,898,167 | 2/1990 | Pierce et al. .................. 128/205.16 |
| 5,125,400 | 6/1992 | Johnson, Jr. . |
| 5,297,944 | 3/1994 | Pomeroy .................. 128/205.13 |
| 5,305,739 | 4/1994 | Gray .................. 128/205.13 |
| 5,388,576 | 2/1995 | Gray .................. 128/205.13 |

FOREIGN PATENT DOCUMENTS

| | | | |
|---|---|---|---|
| 74811 | 1/1961 | France .................. | 128/205.13 |
| U-8700791 | 5/1987 | Germany . | |
| U-8811253 | 11/1988 | Germany . | |
| 18696 | 8/1897 | United Kingdom .................. | 128/205.14 |
| 1550720 | 8/1979 | United Kingdom .................. | 128/205.14 |

Primary Examiner—Kimberly L. Asher
Attorney, Agent, or Firm—Blakely, Sokoloff, Taylor & Zafman

[57] ABSTRACT

A pump that can be adjusted to vary the volumetric output of the pump. The pump has a flexible housing that defines an inner pump chamber. The flexible housing can be collapsed by the user to discharge the contents of the inner chamber. Integral with the housing is an outer spring that returns the pump to the original extended position when the housing is released by the user. The pump further includes one-way valves that allow air to flow into and out of the inner chamber. Wrapped around the housing is a belt that controls the extended volume of the inner chamber and the corresponding volumetric output of the pump. The belt can be adjusted to vary the size of the inner chamber and the volumetric output of the pump. The belt may have different settings that define the amount of air provided by the pump. When used as part of a resuscitator unit, the belt can be adjusted to match the volumetric output of the pump with the lung capacity of the patient.

8 Claims, 4 Drawing Sheets

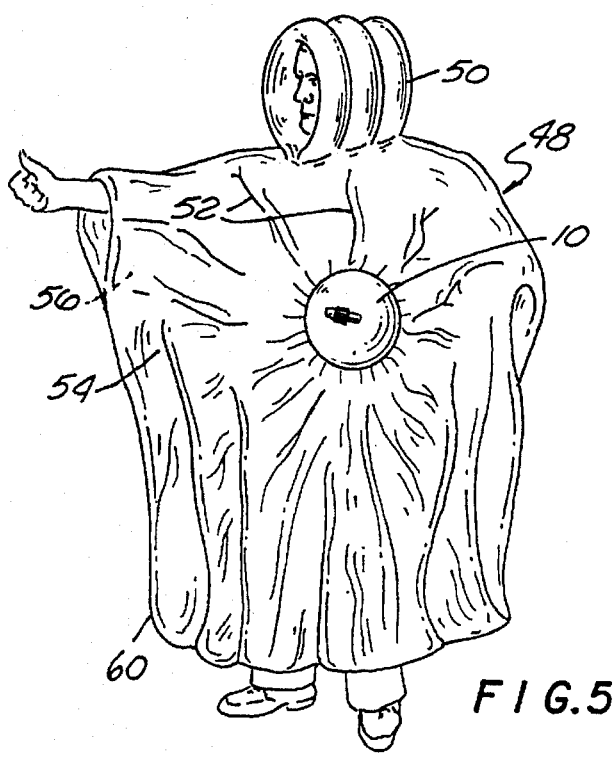
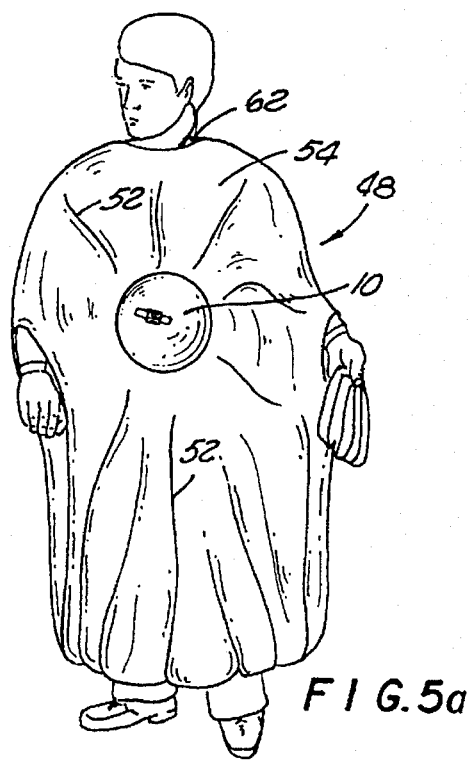
FIG.5   FIG.5a
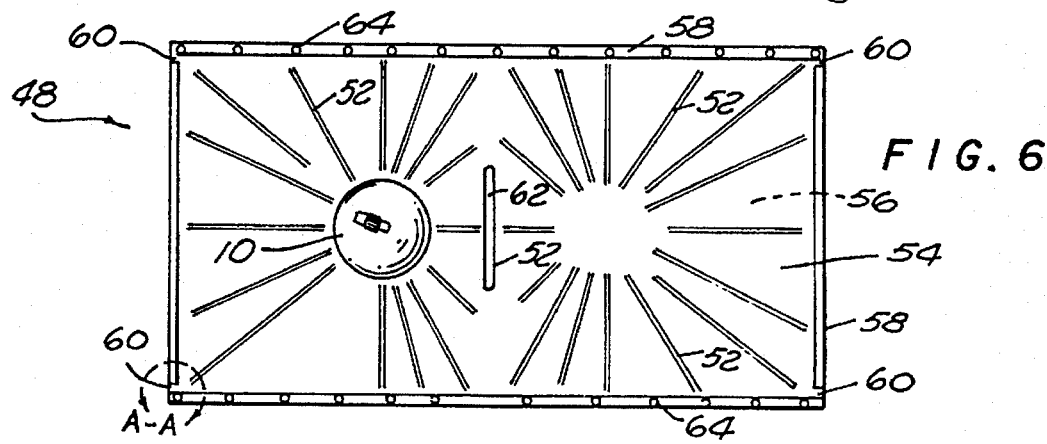
FIG.6
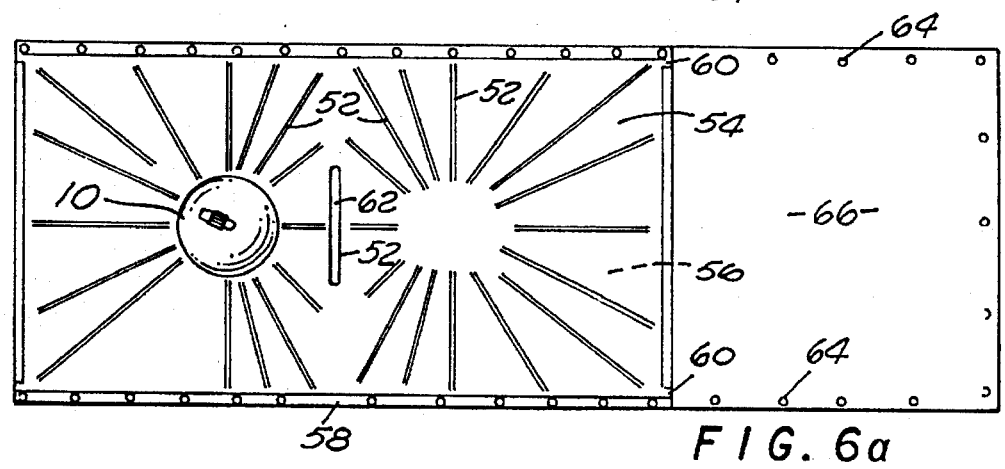
FIG.6a

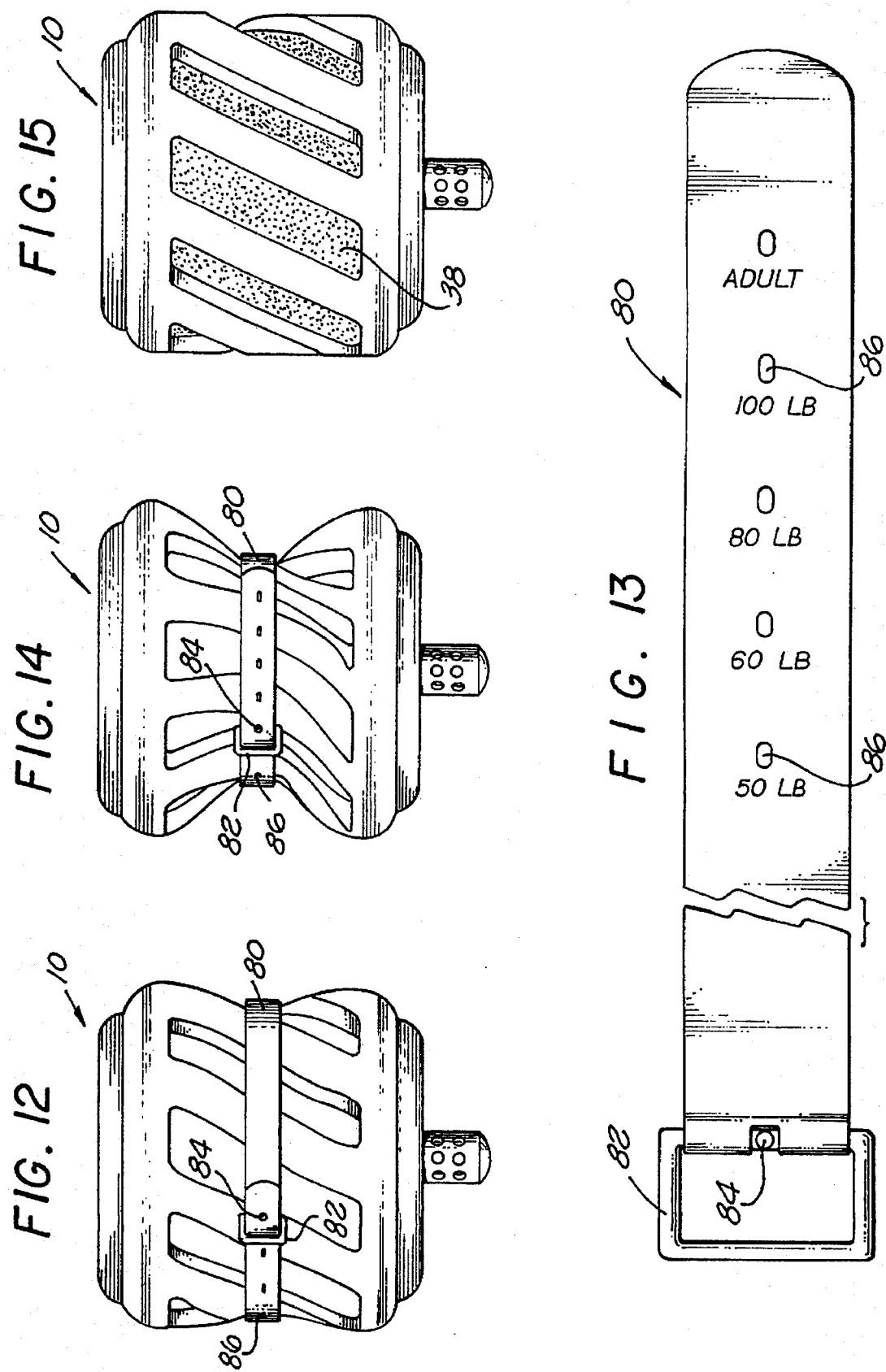

VARIABLE VOLUMETRIC INFLATABLE PUMP

This application is a continuation-in-part of application Ser. No. 07/909,756, filed Jul. 7, 1992, now U.S. Pat. No. 5,297,944.

BACKGROUND OF THE INVENTION

1. Field of the Invention

The present invention relates to a manually operated hand held pump that is coupled to a resuscitator mask.

2. Description of Related Art

Resuscitator units are used to resuscitate someone who is not breathing correctly, or is not breathing at all. A conventional resuscitator unit contains a mask that is placed on the patients face and a pump that is coupled to the mask. The operator pushes air into the patient by squeezing the outer surface of the pump and collapsing the pump housing. The pump typically contains one-way valves that allow the pump chamber to intake and discharge air.

The amount of air received by the lungs of the patient correspond to the volume of the pump chamber. The larger the pump chamber, the more air that is pumped into the patient. Adolescents and infants typically have smaller lungs than an adult. For this reason, conventional resuscitator pumps are provided in three different sizes, infant, adolescent and adult, which each provide a different volumetric output of air.

Resuscitation is frequently administered by paramedic teams that drive to the patient. The resuscitation pumps are stored within the paramedic vehicle. Having to carry three different pumps increases the storage requirements of the resuscitator unit. Additionally, the paramedic team must first identify the size of the patient before selecting the correct pump. The identification and selection process can waste valuable time in aiding the patient. It would be desirable to have a single pump that can be used on any patient, regardless of their size.

SUMMARY OF THE INVENTION

The present invention is a pump that can be adjusted to vary the volumetric output of the pump. The pump has a flexible housing that defines an inner pump chamber. The flexible housing can be collapsed by the user to discharge the contents of the inner chamber. Integral with the housing is an outer spring that returns the pump to the original extended position when the housing is released by the user. The pump further includes one-way valves that allow air to flow into and out of the inner chamber.

Wrapped around the housing is a belt that controls the extended volume of the inner chamber and the corresponding volumetric output of the pump. The belt can be adjusted to vary the size of the inner chamber and the volumetric output of the pump. The belt may have different settings that define the amount of air provided by the pump. When used as part of a resuscitator unit, the belt can be adjusted to match the volumetric output of the pump with the lung capacity of the patient. In operation, the belt can be adjusted to an infant setting when resuscitating an infant, to an adolescent setting when resuscitating an adolescent and so forth and so on.

BRIEF DESCRIPTION OF THE DRAWINGS

The objects and advantages of the present invention will become more readily apparent to those ordinarily skilled in the art after reviewing the following detailed description and accompanying drawings, wherein:

FIG. 5 is an illustration of the novel pump embodied in an inflated poncho and a separate inflated head protector;

FIG. 5a is an illustration of the pump/poncho with both the pump and poncho in the deflated condition;

FIG. 6 is a plan view of the pump/poncho;

FIG. 6a is another plan view of the pump/poncho with an additional section serving as ground cover;

FIG. 12 is a perspective view showing an alternate pump embodiment;

FIG. 13 is a top view of a belt that varies the volumetric output of the pump;

FIG. 14 is a perspective view showing the belt adjusted to constrict the volume of the pump;

FIG. 15 is a perspective view showing an alternate pump embodiment, wherein the inflated spring chambers are filled with a foam material.

DETAILED DESCRIPTION OF THE INVENTION

Figure 1:
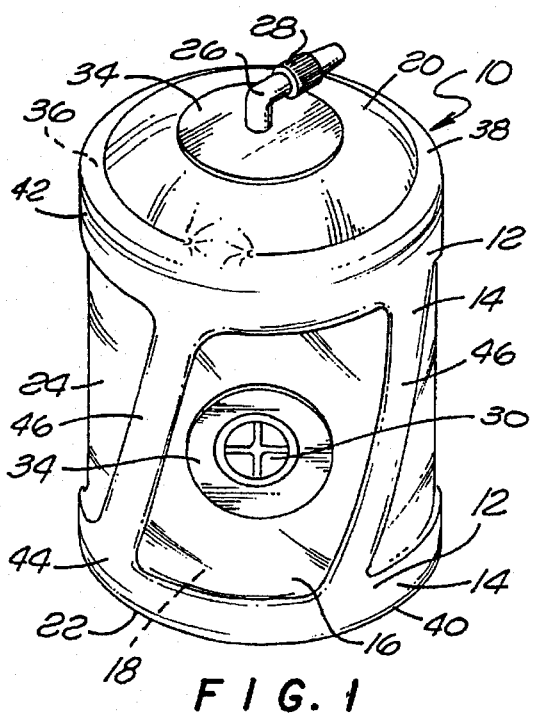
FIG. 1 is an illustration of the novel pump fully inflated and distended.

Referring now to FIG. 1, there is shown a illustrational view of the novel pump 10 in its inflated and extended condition. As indicated, pump unit 10 comprises an inflatable spring framework 12 which serves as the mechanism for returning pump 10 to an extended position on its suction stroke due to the restoring tendency of the inflatable spring framework 12. inflatable spring framework 12 comprises a continuous passage which is formed by an outer layer 14 of lightweight flexible material which is superimposed over underlayer 16 which forms the pumping chamber 18. The pump 10 has an upper end 20, a lower end 22, and a cylindrical side portion 24. In this view, inflatable spring framework 12 has been inflated through the use of inflation nipple 26 and inflation valve 28. Inflation valve 28 is closeable to prevent deflation. As illustrated in FIG. 1, the inflation and distention of inflatable spring framework 12 extends underlayer 16 from its collapsed condition to its expanded and extended position and thereby forms pumping chamber 18. As indicated earlier, pumping chamber 18 is sealed except for the areas where one-way discharge valve 30 and one-way inlet valve 32 are located. Therefore, the volume of fluid which enters through inlet valve 32 into pumping chamber 18 is trapped therein. It can readily be seen that placing one's hands over the pump's lower end 22 and upper end 20 and exerting compressive force will result in the distortion of inflatable spring framework 12 and compression of pumping chamber fluid which was trapped in pumping chamber 18 out through discharge valve 30.

As illustrated, discharge valve 30, inlet valve 32 and inflation valve 28 include an annular flange 34 surrounding said valves which are employed to attach valves to pump 10 and as attachment locations for securing pump 10 to extant inflatable devices but are otherwise superfluous. Discharge valve 30 should be configured to provide a means of attachment to any desired article to be inflated or any transmission means for the expelled fluid. The means of securing pump 10 to the device to be inflated can be by bonding annular flange 34 to the device or by attachable and detachable connection means.

Removing the compressive force allows the pump 10 to return on its suction stroke due to the restoring tendency of the distorted inflatable spring framework 12 and permits inlet valve 32 to open, allowing a fresh charge of fluid to enter pumping chamber 18 to repeat the cycle. It is to be noted that the various valves, i.e. inflation valve 28, discharge valve 30 and inlet valve 32 can be located in positions other than that shown in FIG. 1, without effecting the operability or novelty of pump 10. The main criteria for determining the location of the various valves is the application in which pump 10 is to be utilized. Further, multiple valves may be utilized and more than one type of inflation of inlet or discharge valve may be utilized, depending on the application of the pump 10. Likewise, the size of the pump 10 and inflatable spring framework 12 can vary with application.

Figure 1A:
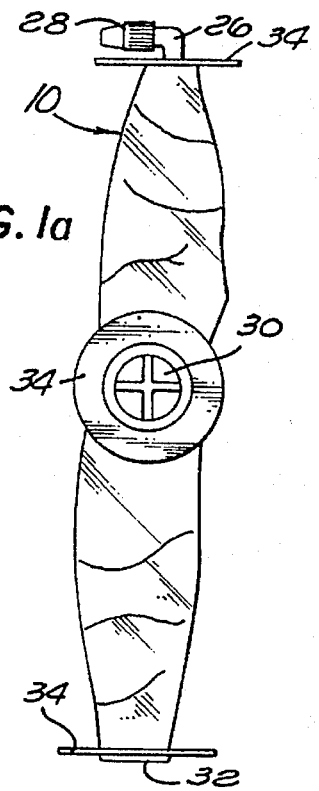
FIG. 1a is an illustration of the pump in the deflated condition.

FIG. 1a is an illustration of the inflatable spring framework 12 and pumping chamber 18 with the inflatable spring framework 12 uninflated. Inflatable spring framework 12 is inflated through the use of inflation nipple 26 and then sealed by closing inflation valve 28. Inflatable spring framework 12 is a hollow, skeletal structure of a particular configuration, integrally attached to pumping chamber 18. Other pump configurations may be utilized, i.e., a sphere, cube, cone frustum, ellipsoid, etc., along with an inflatable spring framework which will provide the above described action. Other configurations of the spring framework can be employed so long as the chosen configuration will have a restoring tendency to provide a pumping chamber in its extended condition and can be collapsed to a compressed position with the creation of restoring tendency, within the inflatable spring framework, back to the extended position.

Figure 2A:
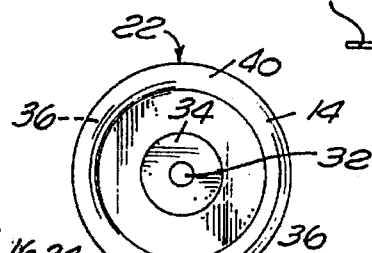
FIG. 2a is a sectional view taken on the line 2A—2A of FIG. 2 showing the inflatable spring framework.
Figure 2:
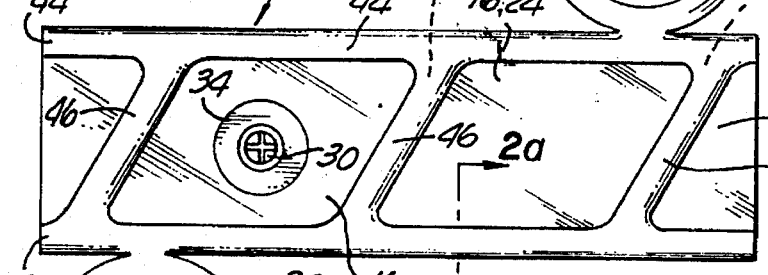
FIG. 2 is a planar layout of the pump prior to final assembly, before it is heat sealed or bonded to form an operable pump.

FIG. 2 is a reduced plan view illustrating the pump assembly 10, inflatable spring framework 12, inflation nipple 26, inflation valve 28, discharge valve 30, inlet valve 32 prior to final assembly. As shown, inflatable spring framework 12 has been created by attaching outer layer 14 to selected portions of underlayer 16 forming passage 36. When fully assembled, pump assembly 10 takes on a generally cylindrical form upon inflation of 12 inflatable spring framework 12. In its collapsed, uninflated condition, it appears as shown in FIG. 1a.

FIG. 2a is a sectional view taken on the line 2A—2A of FIG. 2. The purpose of this view is to give a clear illustration of the relationship of inflatable spring framework 12 to pumping chamber 18. As shown, inflatable spring framework 12 is formed by providing an outer layer 14 of flexible material over selected portions of under layer 16, thus forming a continuous passage 36 therebetween. As pointed out above, passage 36 is one continuous interconnected passage, as more clearly shown in FIG. 2, which when inflated takes on its expanded shape and thereby extends pumping chamber 18 to its expanded shape and simultaneously draws in a charge of fluid through inlet valve 32. As shown in FIGS. 1 & 2, the inflatable spring framework 12 has an upper annulus 38 as part of the upper end 20 and a lower annulus 40 as part of the lower end 22. The upper annulus 38 fluidly communicates with an upper ring 42; while the lower annulus 40 fluidly communicates with the lower ring 44. Extending between the upper ring 42 and the lower ring 44 in fluid communication are a series of parallel, equally spaced columns 46, in this case, three of such columns. The columns 46 extend at an angle of about 60 degrees, intersecting the upper ring 42 and the lower ring 44. Also, the upper end 20 is inflated into a distended dome shape to facilitate passage of fluid from inflation valve 28 into the spring framework through passages 29.

When inflated, the spring framework becomes a self supporting structure, expanding the pump chamber. The internal pressure in the spring framework may vary, for example, if it is expanded orally or by use of a pressurized source. The greater the pressure, the stiffer will be the framework. Also, the amount of force needed to collapse the spring framework to the compressed position of the pump will vary depending on the inflation pressure of the spring framework. Also, the restoring tendency will be greater with greater inflation pressure of the spring framework. Also it should be appreciated that the configuration of the framework will affect its restoring tendency and the force required to collapse it.

Therefore, the inflatable spring framework 12 when inflated will provide a sufficiently ridged framework in its inflated condition to establish the extended cylindrical shape for the pumping chamber 18. When compressed it will exhibit a restoring tendency and return the pump chamber and spring framework to the prior extended position.

Figure 3:
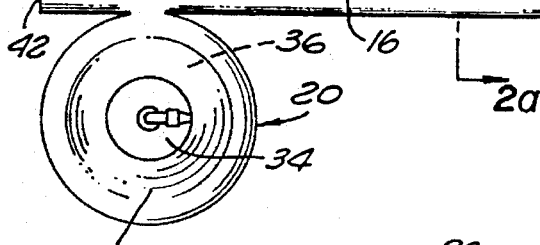
FIG. 3 is an elevational perspective view of the pump per se in a deflated and folded condition.

FIG. 3 is an elevational illustration of the pump and inflatable spring framework deflated and in one configuration of a folded condition. The pump and uninflated spring framework may be folded, rolled, wadded or stowed as the case may require.

Figure 4:
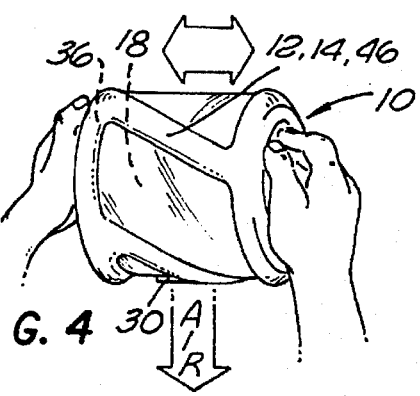
FIG. 4 is an illustration of a manner in which the user may place his hand prior to beginning a pumping stroke.

Referring now to FIG. 4, there is shown an illustration of the manner in which the novel pump 10 is operated. After inflating and distending the inflatable spring framework 12, pump 10 is ready to inflate an article or to be a source for air or other fluid. Placing one's hands over the end portions 20 and 22 of the pump 10 and exerting an compressive force will result in the fluid within pumping chamber 18 being forced out through discharge valve/s 30. Release of the compressive force on pump 10 permits inflatable spring framework 12 to return the pump on its suction stroke to its expanded position due to the restoring tendency, thus recharging pumping chamber 18 with a fresh charge of fluid in preparation for the next pumping stroke. It can readily be seen that repeated operation of the pump in this manner will produce a flow of fluid.

The inlet of many articles to be inflated are provided with a one way inlet valve, in which case, cessation of pumping strokes on pump 10 will leave the article inflated, hence, inflation valve 28 may be opened, allowing inflatable spring framework 12 to deflate and pump 10 may be collapsed and stowed as desired.

Referring now to FIG. 5, there is shown an elevational illustration of a user wearing a poncho 48 which has been inflated with air by the novel pump 10. Additionally, the user is shown wearing an inflated head protector 50. The poncho 48 and head protector 50 are two separate articles with separate pump 10 inflators.

The darker lines 52 represent the lines on which the lower layer 54 and 56, respectively, have been joined together, forming the passage ways through which the fluid from pump 10 flows, inflating poncho 48. It is sufficient to state that FIG. 5 is an illustration of one use to which applicant's new and novel pump 10 may be applied.

FIG. 5a is another elevational illustration of a user wearing poncho 48 which has not been inflated. In the non-inflated condition, the poncho 48 merely drapes over the user's shoulders and is worn as a protector from the rain or other elements. The inflatable spring framework 12 and pump 10 are not inflated.

FIG. 6 is a plan view of poncho 48 in its deflated condition. As illustrated, poncho 48 is comprised of two sheets or layers, 54 ant 56, of impermeable material such as polyurethane or coated rip-stop nylon, having a thickness 0.001 to 0.005 inches and covering an area of approximately five feet by nine feet. Although poncho 48 is comprised of two layers 54 and 56, only upper layer 54 is visible in this view. Upper layer 54 is superimposed over lower layer 56 and both layers are joined and sealed about their periphery 58 and lines 52 by conventionally sealing or bonding the two layers 54 ant 56 together with the exception of four corner areas where over-pressure relief reed type valves 60 are located.

A head opening 62 is located in the center of poncho 48 and is provided with a convention seal 52 around the perimeter of head opening 62 to prevent escape of fluid from between upper and lower layers 54 and 56. Lengthwise sides of poncho 48 are provided with a plurality of fasteners or closure devices 64 which will permit the sides to be closed once the poncho is donned by the user. Located to the left of head opening 62 on the left-hand portion of poncho 48 is the novel pump unit 10.

Referring now to FIG. 6a, there is shown another plan view of a poncho 48 which includes the novel pump 10. The components of this figure are identical to that described above with 6a a ground cover 66 is permanently attached to the rightward end of poncho 48. Ground cover 66 is used to provide protection to the wearer from contact with wet or snowy ground. Additionally, when a first poncho 48 is secured to a second poncho 48 by fasteners 64 to form a pup tent 68, ground cover 66 provides the floor of the tent and a measure of protection from the ground in wet or snow environments. Ground cover 66 is not inflatable. It is merely a single layer of impermeable material which will insulate the user to a degree from the cold or wet ground by providing a barrier therebetween. When ground cover 66 is not in use it is folded inwardly and secured to the inner periphery of the poncho's rigid-hand portion by fasteners 64.

Figure 7:
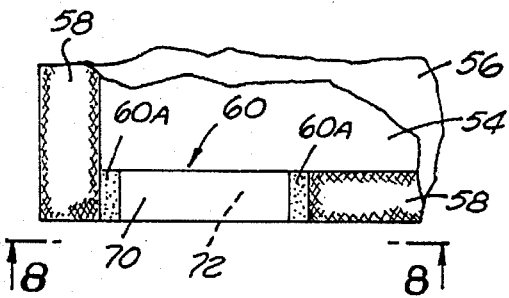
FIG. 7 is an enlarged side view of the pressure relief valve shown in the circle A—A of FIG. 6.

FIG. 7 is a plan view of one of the over pressure relief, reed type valves 60, shown in the circle A—A of FIG. 6. As shown, upper and lower layers 54 and 56 are sealed at 58 with relief valve 60 positioned adjacent to each of the four corners.

Figure 8:
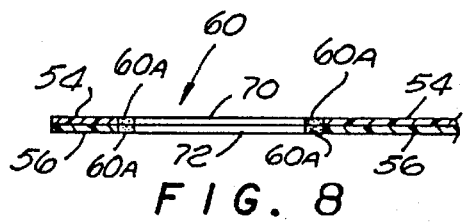
FIG. 8 is an end view of the pressure relief valve, in closed condition, taken on the plane 8—8 of FIG. 7.

FIG. 8 is an end view taken along the plane 8—8 of FIG. 7 illustrating over-pressure relief valve 60 in its closed position. Relief valves 60 comprise a pair of reed-like plastic strips 70 and 72 of heavier gauge than layers 54 and 56 which are secured at their respective ends as shown at 60a.

Although a particular type of inflation valve 28, pressure relief valve 60, one way discharge valve 30 and one way inlet valve 32 are disclosed, any other suitable type of valves may be used for these purposes in other suitable locations.

Figure 9:
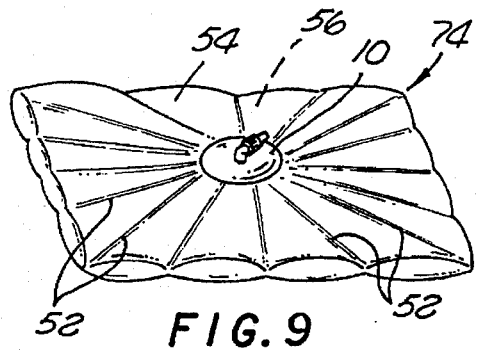
FIG. 9 is a perspective view of an inflatable blanket which is shown in its inflated condition. The novel pump is centrally located beneath the upper layer of the blanket. The relationship of pump with respect to upper and lower layers is the forth in relation to FIGS. 1–4.

FIG. 9 is a perspective view illustration of an inflatable blanket 74 which includes applicant's novel pump 10 integrally mounted therein. The inlet, discharge, pressure relief and inflation valves all function in the same manner as set forth hereinabove. When blanket 74 is properly inflated, it will provide the user with protection from inclement or freezing weather by providing two thermal boundary layers plus a layer of dead-air insulation between the user and the elements.

Blanket 74 is comprised of an upper layer 54 and lower level 56 of material which is impermeable to air. The perimeter is sealed to form a capsule of square or rectangular shape and is inflated in the same manner as poncho 48 described above.

Figure 10:
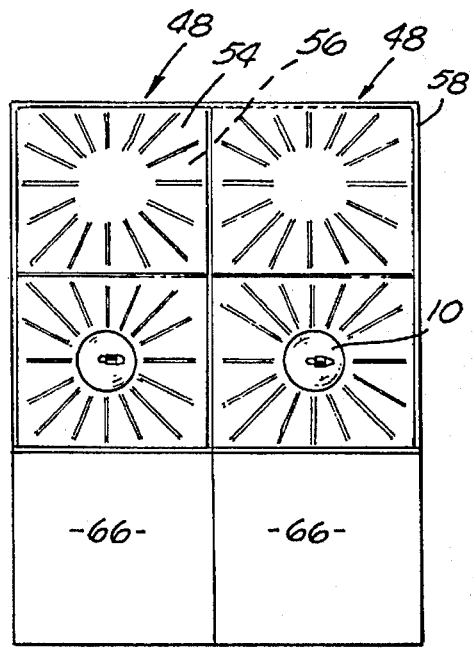
FIG. 10 is a plan view of a pup tent which is comprised of two poncho units and a ground cover attached to each of the units.
Figure 10A:
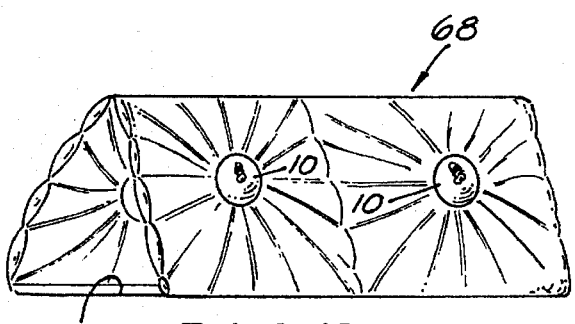
FIG. 10a is a perspective view illustrating pup tent of FIG. 10, in its inflated and erected condition.

FIGS. 10 and 10a are illustrations of plural poncho units 48 secured together by mating fasteners 64 t serve as a pup tent 68. FIG. 10 shows a plan view of pup tent 68 before it is erected or inflated. FIG. 10 is a plan view of a pup tent 68 which is assembled by joining two poncho units 48 in side-by-side relation. The means of attachment can be by zippers, hook and loop strips, snap fasteners or any other suitable means.

FIG. 10a is a perspective view illustrating the pup tent 68 of FIG. 10 inflated and erected. No supporting poles or ropes are illustrated because the inflated ponchos 48 are structurally self supporting. In some instances, depending upon weather conditions, poles and ropes may be required for stability.

Figure 11:
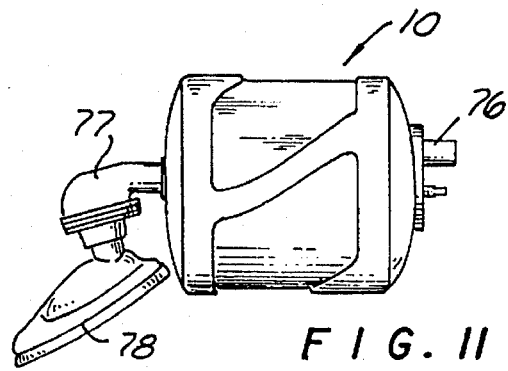
FIG. 11 is a plan view of a resuscitator embodiment of the novel pump shown in its inflated condition with inlet resuscitator valve and non-rebreathing resuscitator outlet valve and resuscitator face mask in place.

FIG. 11 is an elevational illustration of novel pump 10 in a preferred embodiment of a resuscitator with the inlet valve 32 and the outlet valve 30 relocated to opposing ends of novel pump, facilitating the inclusion and application of one-way inlet resuscitator valve 76 and one-way non-rebreathing outlet resuscitator valve 77 and resuscitator face mask 78.

Figure 11A:
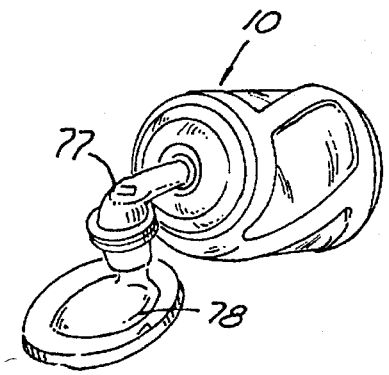
FIG. 11a is a perspective view illustrating the resuscitator embodiment of the novel pump.

FIG. 11a is an additional illustration of novel pump 10 in a embodiment of a resuscitator showing one-way nonrebreathing outlet resuscitator valve 77 and resuscitator face mask 78.

Although a variety of articles have been disclosed, the common denominator of each unit is applicant's novel pump 10. Some of the units can be made of lightweight material and disposed of after a single use, while other embodiments, for example, military versions, would be made of heavier material and reusable as desired. The novel pump 10 may also be used as a stand-alone inflation device when a proper adapter is fitted to discharge valve.

FIG. 12 shows an alternate pump embodiment which has a belt 80 that can be used to vary the volumetric output of the pump 10. The belt 80 wraps around the outer surface of the pump 10. Tightening the belt 80 will reduce the volume of the pumping chamber 18 and the amount of air discharged by the pump 10.

As shown in FIG. 13, the belt 80 may have a buckle 82, a peg 84 and a plurality of holes 86. The belt 80 is fastened by extending an end of the belt through the buckle 82 and inserting the peg 84 through one of the holes 86. The outer layer of the pump may have loops (not shown) that couple the belt 80 to the pump when the belt 80 is in an unfastened position. Although a buckle 82, peg 84 and holes 86 are shown and described, it is to understood that the belt 80 may have other fastening means, such as hook and loop material, which fasten the belt.

The belt 80 may have indicia next to each hole 86 that correlate to the amount of air and corresponding pressure that will be discharged by the pump. By way of example, the indicia and holes 86 may correlate to different masses of air provided by the pump, such as 50 lb., 60 lb., and so forth and so on. When used with a resuscitator mask 78, the belt 80 may have indicia such as "infant", "adolescent" and "adult" which correspond to pump settings for patients that are either infants, adolescents or adults. Alternatively, the indicia may be a combination of pressure values and patient descriptions as shown in FIG. 13. The different pressure settings may corresponds to children of different sizes. For example, the pressure indicia may have corresponding ages such as "60 lb. (ages 8–12)". The adult setting would be used when the resuscitator unit is used on an adult patient.

FIG. 14 shows the pump with the belt 80 adjusted to reduce the volume of the pumping chamber 18. Reducing the volume of the pumping chamber 18 decreases the amount of air that is discharged by the pump 10. The belt 80 thus allows an operator to vary the output of the pump 10. This is particularly advantageous when the pump 10 is part of a resuscitator unit that is used by a paramedic team resuscitating a patient. The present invention allows a paramedic team to carry a single pump that can be used on patients of different sizes. The belt allows the operator to vary the pump output after identifying the size of the patient.

FIG. 15 shows another alternate embodiment, wherein the passage chamber 38 of the inflatable spring framework 12 is filled with a foam material. When the pump is used in a sterile environment, the pump is generally not reusable if the inflatable spring framework 12 is filled with air from a non-sterile environment, such as the lungs of the operator. Filling the chamber 38 with foam provides a pump that can be reused even in a sterile environment. The foam is preferably an open cell material such as a urethane, that can be collapsed and will have enough stiffness to return the pump to the expanded position. As an alternate embodiment, the entire pump may be constructed from a foam material that has an inner liner which seals the pumping chamber 18.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A pump, comprising:

an inflatable housing that has a side portion that joins a pair of end portions, said inflatable housing has a first inflatable ring located at one of said end portions and a second inflatable ring located adjacent to said first inflatable ring, said inflatable housing having a third inflatable ring located at an end opposite from said first inflatable ring, said inflatable housing having a plurality of inflatable springs that extend between said first inflatable ring and said third inflatable ring, said inflatable springs being separated by a plurality of non-inflatable segments and extending at an oblique angle relative to said first and third inflatable rings, said inflatable housing further having an inner chamber;

a valve assembly that allows air to enter and exit said inner chamber of said inflatable housing; and, a port that allows said inflatable spring, said first inflatable ring, said second inflatable ring, and said third inflatable ring to be inflated with air.

2. The pump as recited in claim 1, wherein said inflatable housing has a fourth inflatable ring located adjacent to said third inflatable ring and connected to said inflatable spring.

3. The pump as recited in claim 1, wherein said valve assembly includes a one-way inlet valve and a one-way outlet valve.

4. The pump as recited in claim 1, further comprising a resuscitator mask that is attached to said valve assembly.

5. The pump as recited in claim 1, further comprising a belt that is wrapped around said side portion of said inflatable housing to limit a volume of said inner chamber.

6. The pump as recited in claim 1, wherein said first and second inflatable rings are attached by a common weld seam.

7. The pump as recited in claim 1, wherein said first inflatable tube is in fluid communication with said second inflatable tube.

8. The pump as recited in claim 1, wherein said first inflatable tube has a diameter that is larger than a diameter of said second inflatable tube.

* * * * *